United States Patent [19]

Morris

[11] Patent Number: 4,585,891
[45] Date of Patent: Apr. 29, 1986

[54] PROCESS FOR THE PRODUCTION OF DIHYDROCARBYL OXALATES

[75] Inventor: George E. Morris, Egham, England

[73] Assignee: The British Petroleum Company P.L.C., London, England

[21] Appl. No.: 634,099

[22] PCT Filed: Dec. 15, 1983

[86] PCT No.: PCT/GB83/00334
§ 371 Date: Jul. 20, 1984
§ 102(e) Date: Jul. 20, 1984

[87] PCT Pub. No.: WO84/02340
PCT Pub. Date: Jun. 21, 1984

[30] Foreign Application Priority Data

Dec. 15, 1982 [GB] United Kingdom ............... 8235695

[51] Int. Cl.$^4$ .............. C07C 67/36; C07C 27/00; C07C 29/48
[52] U.S. Cl. .................... 560/204; 560/190; 560/193; 568/909
[58] Field of Search .............. 560/190, 193, 204; 568/909

[56] References Cited

U.S. PATENT DOCUMENTS

| | | | |
|---|---|---|---|
| 3,393,136 | 7/1968 | Fenton et al. | 560/204 X |
| 3,994,960 | 11/1976 | Yamazaki et al. | 560/204 |
| 4,005,128 | 1/1977 | Zehner et al. | 560/204 |
| 4,076,949 | 2/1978 | Zehner | 560/204 |
| 4,160,107 | 7/1979 | Agnes et al. | 560/204 |

Primary Examiner—Natalie Trousof
Assistant Examiner—Vera C. Clarke
Attorney, Agent, or Firm—Brooks Haidt Haffner & Delahunty

[57] ABSTRACT

Dihydrocarbyl oxalates are produced by reacting under substantially anhydrous conditions a dihydrocarbyl peroxide with carbon monoxide in the presence of a catalyst comprising a platinum group metal in compound or elemental form and a copper compound, optionally in the presence as promoter of a heterocyclic aromatic nitrogen compound.

17 Claims, No Drawings

PROCESS FOR THE PRODUCTION OF DIHYDROCARBYL OXALATES

The present invention relates to a process for the production of dihydrocarbyl oxalates.

Dialkyl oxalates have various industrial uses, such as for example, reagents for analysis, solvents, and starting materials for oxamide, orotic acid, etc production. By far their greatest potential use is as an intermediate in the production of ethylene glycol by hydrogenation. Specific dialkyl oxalates are also intermediates in the production of other valuable products. For example di-t-butyl oxalate is known to undergo a facile and efficient decomposition to i-butene and oxalic acid, which latter product is used in industry as a mordant in cloth printing, for the manufacture of dyes, dextrin, ink, as a bleaching agent for straw and as a precipitant for the rare-earths.

Early methods for preparing dialkyl oxalates involved heating anhydrous oxalic acid with an aliphatic alcohol in the presence of concentrated sulphuric acid. Thereafter, in keeping with the trend towards the utilisation of carbon monoxide, either alone or in combination with hydrogen, in the synthesis of bulk organic chemicals, several patents describe the production of dialkyl oxalates by reacting an aliphatic alcohol with carbon monoxide and oxygen in the presence as catalyst of a mixture of a salt of a platinum group metal and a salt of copper or iron. Such patents include U.S. Pat. Nos. 3,391,136 and 3,994,960. Of necessity water is formed when an alcohol is reacted with carbon monoxide and molecular oxygen. It is recognised that the formation of water is undesirable, because it can deactivate the catalyst, it can depress the yield of dihydrocarbyl oxalate and it can complicate product separation. For this reason steps have been taken to remove the water as it is formed by the addition of a dehydrating agent, for example an alkyl orthoformic ester.

More recently, integrated processes for the production of ethylene glycol via the intermediate formation of dialkyl oxalates have been disclosed. Typically, GB 2083032A describes a process for continuously preparing ethylene glycol by (1) a first step of contacting a gas containing carbon monoxide and an ester of nitrous acid with a solid catalyst of the platinum group metal series in the gaseous phase thereby to obtain a product containing a diester of oxalic acid, (2) a second step of condensing the product of the first step thereby to separate a non-condensed gas containing nitrogen monoxide formed by the catalytic reaction of the first step from a condensed liquid containing the diester of oxalic acid, (3) a third step of contacting the non-condensed gas of the second step with a gas containing molecular oxygen and an alcohol, and recycling the resulting gas containing an ester of nitrous acid to the first step, (4) a fourth step of contacting the condensed liquid of the second step containing the diester of oxalic acid and hydrogen with a catalyst for hydrogenation in the gaseous phase thereby to obtain a product containing ethylene glycol, (5) a fifth step of distilling the product of the fourth step thereby to distil out the alcohol and to obtain ethylene glycol, and (6) a sixth step of recycling the alcohol of the fifth step as an alcohol source for the third step. In this process nitrogen monoxide functions essentially as a carrier for oxygen. Whilst nitrogen monoxide may be effective as an oxygen carrier, it can under certain conditions, eg the presence of water, cause corrosion of plant and associated equipment with which it comes into contact.

Canadian Pat. No. 743559 describes a method of producing a tertiary ester of a carboxylic acid comprising contacting with agitation carbon monoxide and a di-t-hydrocarbyl peroxide of the formula (RR'R")C—O—O—C(RR'R") wherein R, R' and R" are hydrocarbyl radicals selected from the group consisting of alkyl, aryl, alkaryl and aralkyl having up to nine carbon atoms, said contacting being conducted at an elevated temperature and carbon monoxide pressure and in the presence of inert organic liquid diluent. The use of transition metal salts as catalysts is said to be desirable for optimum yields of ester. Specific examples of transition metal salts contemplated are said to be halides, carboxylates and nitrates of copper, cobalt, manganese, iron and vanadium.

We have now found a route to dialkyl oxalates via the reaction of a dihydrocarbyl peroxide with carbon monoxide, and hence to ethylene glycol, which avoids the formation of water together with its associated disadvantages. The route also avoids the formation and use of nitrogen monoxide and the use of molecular oxygen, thereby minimising the risk of explosion.

Accordingly, the present invention provides a process for the production of a dihydrocarbyl oxalate which comprises reacting under substantially anhydrous conditions a dihydrocarbyl peroxide with carbon monoxide in the presence of a catalyst comprising a platinum group metal in compound or elemental form and a copper compound.

The term "hydrocarbyl" is used throughout this specification in the commonly accepted sense as denoting the moiety formed by the removal of a hydrogen atom from a hydrocarbon.

With regard to the dihydrocarbyl peroxide, the dihydrocarbyl radical may suitably be an alkyl, aryl, alkaryl or aralkyl group having up to 9 carbon atoms, and may be the same or different. Suitable peroxides include di-cumyl peroxide and di-tertiary-butyl peroxide (DTBP), of which DTBP is preferred. DTBP may readily be obtained, for example by reacting t-butanol with t-butyl hydroperoxide, which in turn may readily be obtained by oxidation of isobutane. A suitable process for producing DTBP is described in U.S. Pat. No. 2,862,973.

Whilst the carbon monoxide employed may contain impurities such as nitrogen, it is preferred that it be substantially pure. Suitably, a substantial excess of gaseous carbon monoxide may be employed. Maintenance of an excess may suitably be accomplished by keeping the reaction system under a carbon monoxide pressure, suitably greater than 15 bars. Although high pressures may be employed if desired, a pressure below 100 bars is preferred.

As catalyst there is used a mixture of a platinum group metal, ie palladium, platinum, rhodium, ruthenium or iridium in elemental or compound form, and a copper compound. Preferably the platinum group metal is palladium. Suitable compounds of the metals include chlorides, nitrates, sulphates, phosphates, alkoxides, acetylacetonates and acetates. The copper compound may suitably be a salt, preferably a halide, for example copper (I) chloride or copper (I) bromide. Typically the catalyst may be a mixture of copper (I) chloride and palladium (II) acetylacetonate. The amount of the catalyst and the relative proportions of the palladium group metal and the copper compounds may vary over a moderately wide range.

In addition to the catalyst a promoter may be employed. Suitably the promoter may be a heterocyclic aromatic nitrogen-containing compound, which may suitably be pyridine or a derivative thereof, for example 2,6-dimethyl pyridine. Furthermore the platinum group metal component of the catalyst may be supported on an inert support. Suitably the inert support may be silica, alumina, silica/alumina, charcoal, graphite, etc.

The process is preferably carried out in the liquid phase. In the liquid phase an inert diluent may suitably be employed. Suitable inert diluents include cyclohexane and acetone, and the like.

The reaction is thought to be represented by the following equation:

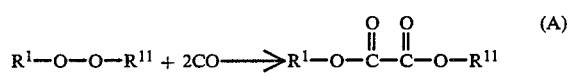

(A)

wherein $R^1$ and $R^{11}$ represent the aforesaid hydrocarbyl groups.

In a preferred embodiment, the dihydrocarbyl peroxide is reacted with carbon monoxide and an alcohol. The alcohol may be an alkanol, a glycol, a polyalkylene glycol or an aryl alcohol. The alcohol may suitably be an alkanol. Examples of suitable alkanols include methanol, ethanol, n-propanol iso-propanol and t-butanol.

In the presence of an alcohol, the reaction in its simplest form is thought to be represented by the following equation:

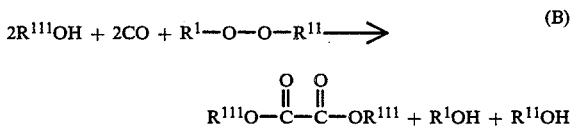

(B)

wherein $R^1$ and $R^{11}$ are hydrocarbyl groups and $R^{111}$ is the hydrocarbyl moiety of an alcohol as hereinbefore described. It will be appreciated by those skilled in the art that dihydrocarbyl oxalates may be produced according to both equations (A) and (B) and that the nature of the oxalate or oxalates actually obtained will depend to some extent on the type of reactant and the reaction conditions employed.

As regards the reaction conditions, reference has already been made to the carbon monoxide partial pressure. The temperature may suitably be above ambient temperature. The specific temperature to be employed will depend, amongst other factors, upon the amount of catalyst and promoter, if any, used. Generally, the rate of the reaction will increase with increasing catalyst and promoter concentration. Within any constraint imposed by control of the reaction temperature, for the reaction is highly exothermic, the catalyst may be employed in an amount up to and beyond stoichiometric and there is no restriction on the amount of promoter which may be used. It will usually be found convenient to employ a temperature greater than 50° C., for example in the range from 80° to 150° C.

Reactions of particular interest include:

(i) The liquid phase reaction of an alkanol comprising methanol, ethanol or iso-propanol with DTBP and carbon monoxide to produce respectively dimethyl, diethyl, or di-isopropyl oxalate and t-butanol. There may also be produced the corresponding dialkyl carbonate, the ratio of alkyl oxalate to dialkyl carbonate in the product being dependent on such factors as the partial pressure of carbon monoxide, the ratio of the catalyst components, the promoter concentration and the temperature. The dialkyl oxalate may be recovered from the product by conventional procedures, for example by cooling or by distillation. t-Butanol may be recovered from the product for use as or conversion into, for example, a fuels supplement, or it may be dehydrated to produce isobutylene and the resulting isobutylene hydrogenated to produce isobutane feedstock for conversion into DTBP. The dialkyl oxalate may suitably be converted into ethylene glycol by hydrogenation. A suitable hydrogenation process is described in U.S. Pat. No. 4,112,245, which is incorporated herein by reference.

(ii) the liquid phase reaction of DTBP with carbon monoxide in the presence of t-butanol to produce di-t-butyl oxalate. The di-t-butyl oxalate may be recovered and decomposed to i-butene which may be separated, converted to DTBP and recycled as DTBP to the process, and oxalic acid which may be recovered. Alternatively, the recovered di-t-butyl oxalate may be converted by conventional means into useful products. t-Butanol may be recovered and recycled to the process.

The process of the invention may be operated batchwise or continuously, preferably continuously.

The invention will now be illustrated by reference to the following Examples.

EXAMPLE 1

An autoclave was charged with methanol (32 ml), di-tertiary-butyl-peroxide (14.5 ml), pyridine (1 ml), cuprous chloride (0.10 gm) and palladium acetylacetonate (0.015 gm). Carbon monoxide gas was introduced to a pressure of 65 bar at 25° C. The mixture was heated to 120° C., with stirring, over a period of 25 minutes. An exothermic reaction took place, the temperature of the mixture reaching a maximum value of 126° C. after a further 9 minutes while the recorded pressure decreased. The reaction mixture returned to 120° C. during 8 minutes and this temperature was maintained for a further 10 minutes. After cooling to room temperature the $^1$H n.m.r. spectrum of the product mixture showed a molar ratio of tertiary butanol:methanol:dimethyl carbonate:dimethyl oxalate of 1:4.2:0.21:0.19 as well as traces of methyl acetate and acetone.

EXAMPLE 2

An autoclave was charged with di-tertiary-butyl peroxide (20.4 gm), acetone (20.1 gm), pyridine copper methoxy chloride (0.28 gm) and palladium (II) acetylacetone (0.043 gm). Carbon monoxide gas was introduced to a pressure of 36 bar at ambient temperature. The mixture was heated, with stirring, to 105° C. and maintained at this temperature for 2 h. During this time further carbon monoxide gas was introduced as necessary to maintain a pressure between 46 and 51 bar. After cooling to ambient temperature the mixture was analysed by gas chromatogrphy and $^1$H nmr. The major components were di-tertiary butyl oxalate (17.4 gm), acetone and tertiary-butanol. The mixture also contained small amounts of other compounds including residual di-tertiary-butyl peroxide (0.8 gm).

Comparative Test

An autoclave was charged with di-tertiary-butyl peroxide (20.4 gm), acetone (20.1 gm), pyridine copper methoxy chloride (0.29 gm), palladium (II) acetylacetonate (0.043 gm) and water (2.2 gm). Carbon monoxide gas was introduced to a pressure of 38 bar at ambient temperature. The mixture was heated, with stirring, to 105° C. and maintained at this temperature for 15 h. During this time further carbon monoxide gas was introduced as necessary to maintain a pressure between 46 and 51 bar. After cooling to ambient temperature the mixture was analysed by gas chromatography and $^1H$ nmr. The major components were acetone, tertiary-butanol and residual di-tertiary butyl peroxide (8.1 gm). No di-tertiary-butyl oxalate was detected.

This is not an example according to the present invention and is included only for the purpose of comparison.

EXAMPLE 3

An autoclave was charged with di-tertiary-butyl peroxide (20.4 gm), tertiary butanol (10.5 gm), pyridine copper methoxy chloride (0.29 gm), palladium (II) acetylacetonate (0.042 gm). Carbon monoxide gas was introduced to a pressure of 21 bar at ambient temperature. The mixture was heated, with stirring, to 80° C. and maintained at this temperature for 19 h. During this time further carbon monoxide gas was introduced as necessary to maintain a pressure between 20 and 26 bar. After cooling to ambient temperature dichloromethane (33.0 gm) was added and the mixture was analysed by gas chromatography and $^1H$ nmr. In addition to tertiary-butanol it contained di-tertiary butyl oxalate (23.8 gm) and small amounts of other compounds including residual di-tertiary-butyl peroxide (0.7 gm).

EXAMPLE 4

An autoclave was charged with di-tertiary-butyl peroxide (17.5 gm), ethanol (16.6 gm), cuprous chloride (0.24 gm), pyridine (0.57 gm) and palladium (II) acetylacetonate (0.036 gm). Carbon monoxide gas was introduced to a pressure of 33 bar at ambient temperature. The mixture was heated, with stirring, to 100° C. and maintained at this temperature for 8 h. During this time further carbon monoxide gas was introduced as necessary to maintain a pressure between 75 and 100 bar. After cooling to ambient temperature the mixture was analysed by gas chromatography. The major components were tertiarybutanol, diethyl oxalate (12.8 gm), ethanol and diethyl carbonate (2.0 gm).

EXAMPLE 5

An autoclave was charged with di-tertiary-butyl peroxide (20.4 gm), methanol (13.4 gm), pyridine copper methoxy chloride (0.59 gm), palladium (II) acetylacetonate (0.041 gm). Carbon monoxide gas was introduced to a pressure of 32 bar at ambient temperature. The mixture was heated, with stirring, to 95° C. and maintained at this temperature for 5 h. During this time further carbon monoxide gas was introduced as necessary to maintain a pressure between 42 and 51 bar. After cooling to ambient temperature methanol (26.8 gm) was added and the mixture analysed by gas chromatography and $^1H$ nmr. The major components were methanol, tertiary-butanol, dimethyl oxalate (10.7 gm) and dimethyl carbonate (2.0 gm).

I claim:

1. A process for the production of a dihydrocarbyl oxalate which process comprises reacting, under substantially anhydrous conditions and at a temperature above ambient, a dihydrocarbyl peroxide with carbon monoxide in the presence of an effective amount of a catalyst comprising palladium in elemental or compound form and a copper compound.

2. A process according to claim 1 wherein the dihydrocarbyl radical of the dihydrocarbyl peroxide is an alkyl, aryl, alkaryl or aralkyl group having up to 9 carbon atoms.

3. A process according to either claim 1 or claim 2 wherein the dihydrocarbyl peroxide is di-tertiary-butyl peroxide.

4. A process according to claim 1 wherein in the copper compound is a halide.

5. A process according to claim 1 wherein a heterocyclic aromatic nitrogen-containing compound is employed as a promoter.

6. A process according to claim 5 wherein the heterocyclic nitrogen-containing compound is pyridine or a derivative thereof.

7. A process according to claim 1 wherein an alcohol is an additional reactant.

8. A process according to claim 7 wherein the alcohol is an alkanol.

9. A process according to either claim 7 or claim 8 wherein di-tertiary-butyl peroxide is reacted in the liquid phase with carbon monoxide and an alkanol which is either methanol, ethanol or isopropanol to produce tertiary-butanol and respectively either dimethyl, diethyl or diisopropyl oxalate.

10. A process according to claim 8 wherein di-tertiary-butyl peroxide is reacted in the liquid phase with carbon monoxide in the presence of t-butanol to produce di-tertiary-butyl oxalate.

11. A process according to claim 1, which is conducted as a liquid phase reaction.

12. A process according to claim 1, wherein the temperature is greater than 50° C.

13. A process according to claim 1, wherein the temperature is in the range of from 80° C. to 150° C.

14. A process according to claim 1, wherein the palladium is in metal form or is in compound form selected from the group consisting of chloride, nitrate, sulphate, phosphate, alkoxide, acetylacetonate and acetate.

15. A process according to claim 5, wherein the copper halide is copper (I) chloride or copper (I) bromide.

16. A process according to claim 6, wherein the promoter is selected from the group consisting of pyridine, 2,6-dimethyl pyridine, and pyridine copper methoxy chloride.

17. A process according to claim 1, wherein the carbon monoxide pressure is greater than 15 bars up to below 100 bars.

* * * * *

UNITED STATES PATENT AND TRADEMARK OFFICE
CERTIFICATE OF CORRECTION

PATENT NO. : 4,585,891

DATED : April 29, 1986

INVENTOR(S) : GEORGE E. MORRIS

It is certified that error appears in the above-identified patent and that said Letters Patent is hereby corrected as shown below:

In The Claims:

Claim 15, col. 6, line 53, "according to claim 5" should read -- according to claim 4 --

Claim 16, col. 6, line 55, "according to claim 6" should read -- according to claim 5 --

Signed and Sealed this

Twenty-third Day of September 1986

[SEAL]

Attest:

DONALD J. QUIGG

Attesting Officer

Commissioner of Patents and Trademarks